US008000796B2

(12) United States Patent
Tass et al.

(10) Patent No.: US 8,000,796 B2
(45) Date of Patent: Aug. 16, 2011

(54) METHOD AND DEVICE FOR DECOUPLING AND/OR DESYNCHRONIZING NEURAL BRAIN ACTIVITY

(75) Inventors: Peter Tass, Titz (DE); Oleksandr Popovych, Düren (DE); Christian Hauptmann, Stolberg (DE); Valerii Krachkovskyi, Jülich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 850 days.

(21) Appl. No.: 11/604,284

(22) Filed: Nov. 27, 2006

(65) Prior Publication Data

US 2007/0203532 A1 Aug. 30, 2007

Related U.S. Application Data

(63) Continuation of application No. PCT/DE2005/000780, filed on Apr. 28, 2005.

(30) Foreign Application Priority Data

May 27, 2004 (DE) .......................... 10 2004 025 945

(51) Int. Cl.
*A61N 1/372* (2006.01)
(52) U.S. Cl. ........................................... 607/45; 607/46
(58) Field of Classification Search .................... 607/45, 607/46
See application file for complete search history.

(56) References Cited

U.S. PATENT DOCUMENTS

| 4,712,558 | A | 12/1987 | Kidd et al. |
|---|---|---|---|
| 6,366,813 | B1 | 4/2002 | DiLorenzo |
| 6,459,936 | B2 | 10/2002 | Fischell et al. |
| 6,480,743 | B1 * | 11/2002 | Kirkpatrick et al. ........... 607/45 |
| 6,529,774 | B1 | 3/2003 | Greene |
| 6,944,501 | B1 | 9/2005 | Pless |
| 2002/0072770 | A1 | 6/2002 | Pless |
| 2002/0077670 | A1 | 6/2002 | Archer et al. |

FOREIGN PATENT DOCUMENTS

| CA | 2479046 | 9/2003 |
|---|---|---|
| DE | 102 11 765 A1 | 10/2003 |
| DE | 102 11 766 A1 | 10/2003 |
| DE | 102 33 960 A1 | 2/2004 |
| DE | 103 18 071 A1 | 11/2004 |
| EP | 1 405 652 A2 | 4/2004 |
| WO | 03/077985 | 9/2003 |

(Continued)

OTHER PUBLICATIONS

Peter A. Tass "Desynchronizing double-pulse phase resetting and application to deep brain stimulation", Biological Cybernetics, vol. 85, No. 5, Nov. 2001, pp. 343-354, XP002245895, ISSN: 0340-1200.

(Continued)

*Primary Examiner* — Scott M Getzow
*Assistant Examiner* — Joseph M Dietrich

(57) ABSTRACT

A device for decoupling and/or desynchronizing neural, pathologically synchronous brain activity, in which, the activities in a partial region of a brain area or a functionally associated brain area are stimulated by means of an electrode, resulting in decoupling and desynchronizing the affected neuron population from the pathological area and suppression of the symptoms in a patient. In an alternative embodiment of the device, the pathologically synchronous brain activity due to the disease is desynchronized which also leads to the symptoms being suppressed. The device has a stimulation electrode and at least one sensor which are driven by a control system in such a manner that they produce decoupling and/or desynchronization in their local environment.

9 Claims, 4 Drawing Sheets

FOREIGN PATENT DOCUMENTS

| | | |
|---|---|---|
| WO | 2004/016165 A1 | 2/2004 |
| WO | WO 2005/053787 A1 | 6/2005 |

OTHER PUBLICATIONS

Peter A. Tass et al., "Obsessive-Compulsive Disorder: Development of Demand-Controlled Deep Brain Stimulation with Methods from Stochastic Phase Resetting", *Neuropsychopharmacology* (2003), vol. 28, pp. S27-S34.

International Search Report (Form PCT/ISA/210) of International Application No. PCT/DE2005/000780, Date of Mailing of the International Search Report: Sep. 5, 2005.

Office Action mailed Sep. 25, 2009; U.S. Appl. No. 11/441,251.

Final Office Action mailed Mar. 20, 2009; U.S. Appl. No. 11/441,251.

Final Office Action mailed Dec. 3, 2009; U.S. Appl. No. 11/441,251.

Office Action mailed Feb. 26, 2008; U.S. Appl. No. 11/441,251.

Office Action mailed on Apr. 16, 2010 in related U.S. Appl. No. 11/441,251.

U.S. Appl. No. 11/441,251, filed May 26, 2006, Method and apparatus for desynchronization of neural brain activity, Forschungszentrum Juelich GMBH, Juelich, Germany.

\* cited by examiner

METHOD AND DEVICE FOR DECOUPLING AND/OR DESYNCHRONIZING NEURAL BRAIN ACTIVITY

CROSS-REFERENCE TO RELATED APPLICATIONS

This application is a continuing application, filed under 35 U.S.C. §111(a), of International Application PCT/DE2005/000780, filed on Apr. 28, 2005, it being further noted that priority is based upon German Patent Application 10 2004 025 945.3, filed on May 27, 2004, the contents of which are incorporated herein by reference.

BACKGROUND OF THE INVENTION

The invention relates to a device for decoupling and/or desynchronizing neural brain activity.

SUMMARY OF THE INVENTION

Additional aspects and/or advantages of the invention will be set forth in part in the description which follows and, in part, will be apparent from the description, or may be learned by practice of the invention.

A pathologically synchronous brain activity which can have its origin, for example, in the basal ganglia, can also produce synchronization in the following areas such as, for example, the motor cortex, as a driving force. This secondary synchronization is significantly involved in generating the pathological symptoms. The invention relates to a device which allows the driving pathological activity to be decoupled from the following areas by which means a great reduction in the pathological symptoms can be effected. In a further embodiment, the device according to the invention can also be used for desynchronizing, i.e. for suppressing a rhythmic collective activity or, respectively, collective firing of the neurons of the pathologically synchronous nerve cell populations, which are called driving populations.

In patients with neurological or psychiatric diseases, e.g. Parkinson's disease, essential tremor, dystonia or compulsive diseases, nerve cell populations are pathologically active, e.g. excessively synchronous, in defined areas of the brain, e.g. the thalamus and the basal ganglia. In this case, a large number of neurons form synchronous action potentials; the neurons involved are firing excessively synchronously. In the healthy person, in contrast, the neurons are firing qualitatively differently in these brain regions, e.g. in an uncorrelated manner. The pathologically synchronous brain activity changes the neural activity in other brain regions, e.g. in areas of the cerebral cortex such as the primary motor cortex. The pathologically synchronous activity then forces its rhythm onto the cerebral cortex areas in the area of the thalamus and of the basal ganglia so that, finally, the muscles controlled by these areas develop pathological activity, e.g. a rhythmic trembling (tremor).

In patients who can no longer be treated by medicaments, a depth electrode is implemented unilaterally or bilaterally depending on the symptoms and on whether the disease occurs unilaterally or bilaterally. In this arrangement, a cable leads under the skin from the head to the so-called generator which comprises a control device with a battery and is implanted underneath the skin, for example in the area of the clavicle. A continuous stimulation with a high-frequency periodic sequence (pulse train with a frequency of >100 Hz) of single pulses, e.g. rectangular pulses, is carried out via the depth electrodes. This method has the aim of suppressing the firing of the neurons in the target areas. The effective mechanism on which the standard depth stimulation is based has not yet been explained sufficiently. The results of a number of studies indicate that the standard depth stimulation acts like a reversible lesion, i.e. like a reversible elimination of the tissue. The standard depth stimulation suppresses the firing of the neurons in the target regions and/or the associated brain areas.

The disadvantageous feature of this form of stimulation is that the energy consumption of the generator is very high so that the generator and its battery must frequently be operatively replaced after only approximately one to three years. It is even more disadvantageous that the continuous high-frequency stimulation, as an unphysiological (unnatural) input in the area of the brain, e.g. the thalamus or the basal ganglia, respectively, can lead to an adaptation of the nerve cell populations affected in the course of a few years. To achieve the same stimulation result, it is then necessary to stimulate with higher stimulus amplitude due to this adaptation. The greater the stimulus amplitude, the greater the possibility that side effects occur due to the stimulation of neighboring areas—such as dysarthria (speech disturbances), disesthesia (in some cases very painful abnormal sensations), cerebellar ataxia (inability to stand securely without aid) or schizophrenic symptoms etc. These side effects cannot be tolerated by the patient. In these cases, the treatment, therefore, loses its effectiveness after a few years.

In other stimulation methods as described, for example, in DE 102 11 766 A1, it is proposed that stimuli are applied in the respective target region controlled by requirement. It is the aim of these methods and these devices, to not simply suppress the pathologically synchronous firing as in the case of the standard depth stimulation but to bring it closer to the physiological uncorrelated firing pattern. By this means, the current consumption is to be reduced, on the one hand, and, on the other hand, the energy input into the tissue is to be reduced by the demand-controlled stimulation in comparison with the standard depth stimulation.

The abovementioned stimulation methods require the use of one or more depth electrodes which represents a high operative effort and a high risk of complications such as, e.g. possible brain tissue damage or brain bleeding during the implantation of the depth electrodes for the patient. However, this risk should be reduced with a view to successfully healing the patient and reducing side effects.

It is an object of the invention, therefore to create a device for decoupling and/or desynchronizing neural brain activity by means of which patients with pathologically synchronized brain activity can be treated mildly and efficiently. In this context, an adaptation to an unphysiological permanent stimulus should be prevented. Longwinded calibration processes should be prevented and the stimulation should also be successful when the main frequency component of the pathologically rhythmic activity is subject to great fluctuations. Furthermore, the device should achieve permanent decoupling and/or desynchronization, and transient stimulation-related unphysiological states should be largely avoided. The device according to the invention does not require additional demand control which, as described in section 6.3, can be optionally added, which is why it is technically easily implemented and only low demands are made on the complexity of the control electronics and thus also on the current consumption. The stimulation device according to the invention is intended to operate in a current-saving manner so that the batteries of the stimulator implanted in a patient need to be replaced operatively less frequently. Since an implantation of preferably only one electrode is necessary and since this electrode is implanted in a following and thus possibly more easily accessible brain area such as, e.g. an epicortical electrode in the area of the motor cortex, the device according to the invention represents a considerable improvement in comparison with the abovementioned methods of depth brain stimulation. This is because the brain stimulation does not require a depth electrode—particularly in a particular embodiment of the device according to the invention, so that there is no risk of intraoperative bleeding due to an injury to an artery.

On the basis of the preamble of claim 1, the object is achieved, according to the invention, by the features specified in the characterizing clause of claim 1. By using the measured and processed activity of the neuron population to be decoupled and/or to be desynchronized as a feedback stimulation signal, see section 3, the object is surprisingly achieved in that the neurons are in each case influenced in their activity by the stimulation with the feedback stimulation signal by means of an electrode, in such a manner that a complete decoupling and/or desynchronization of the neutron population to be decoupled from the driving pathological neuron population occurs surprisingly as a result of which the symptoms are surprisingly suppressed in a patient. In a further embodiment of the device according to the invention as described in section 8, the device can also be used, for example, for desynchronizing the driving neuron population. In this embodiment, the measured and processed neural activity of the driving neuron population is applied as feedback stimulation signal via the stimulation electrode so that a direct or indirect stimulation of the driving neuron population with the feedback stimulation signal occurs. By this means, the neuron population to be desynchronized is influenced in such a manner that a complete desynchronization occurs surprisingly, as a result of which the disease-related symptoms are suppressed. For this purpose, the device according to the invention comprises a control system 4 which receives the measurement signal of the sensors 3 or of the sensors 3 and generates from this signal a stimulation signal and applies it to the electrode 2 as stimulation stimulus.

The device according to the invention operates in a current-saving manner so that batteries implanted in the patient need to be replaced less frequently.

The device according to the invention enables the effect achieved intraoperatively by means of the decoupling stimulation to be used for selecting the most suitable target point for the electrode. When using a depth brain electrode as electrode 2, a test stimulus and/or derivation of the feedback signal is first carried out in mm steps with the device according to the invention in the area of the anatomically precalculated target point during the implantation of the electrode. The target point at which the best therapeutic effect can be achieved is selected as target point for the permanent implantation.

Apart from the abovementioned diseases which exhibit frequently persistent pathologically synchronous activity with relatively constant frequency, diseases can also be treated in which pathologically synchronous activity only occurs intermittently (occurring for short times). A main indication is the treatment of epilepsies which can no longer be treated by medicaments. The device according to the invention can effect a suppression of the symptoms, for example, in the illnesses Parkinson's disease, essential tremor, dystonia, epilepsy, depression and compulsive diseases.

Advantageous developments of the invention are specified in the subclaims.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2a shows the variation with time of the neural activity, measured via sensor 3, of the neuron population to be decoupled during the uncoupled state, during the coupling and during the stimulation.

FIG. 2b shows the variation with time of the firing pattern of the neuron population to be decoupled during the uncoupled state, during the coupling and during the stimulation.

FIG. 2c shows the variation with time of the extent of synchronization of the neuron population to be decoupled during a stimulation interval. Small values correspond to little synchronization and large values correspond to strong synchronization.

FIG. 2d shows variation with time of the resultant influence of stimulation on the neuron population to be decoupled, i.e. the sum of the coupling and stimulation influences.

FIG. 2e shows distribution of firing frequencies before the coupling (on the left), during the coupling (center) and with stimulation switched on (on the right).

FIG. 3a shows the variation with time of the neural activity, measured via sensor 3, of the neuron population to be decoupled during the uncoupled state, during the coupling and during the stimulation.

FIG. 3b shows the variation with time of the firing pattern of the neuron population to be decoupled during the uncoupled state, during the coupling and during the stimulation.

FIG. 3c shows the variation with time of the extent of synchronization of the neuron population to be decoupled. Small values correspond to little synchronization and large values correspond to strong synchronization.

FIG. 3d shows the variation with time of the resultant influence of stimulation on the neuron population to be decoupled, i.e. the sum of the coupling and stimulation influences.

FIG. 3e shows the distribution of the firing frequencies before the coupling (on the left), during the coupling (center) and with the stimulation switched on (on the right).

DETAILED DESCRIPTION OF THE PREFERRED EMBODIMENTS

Figure 1:
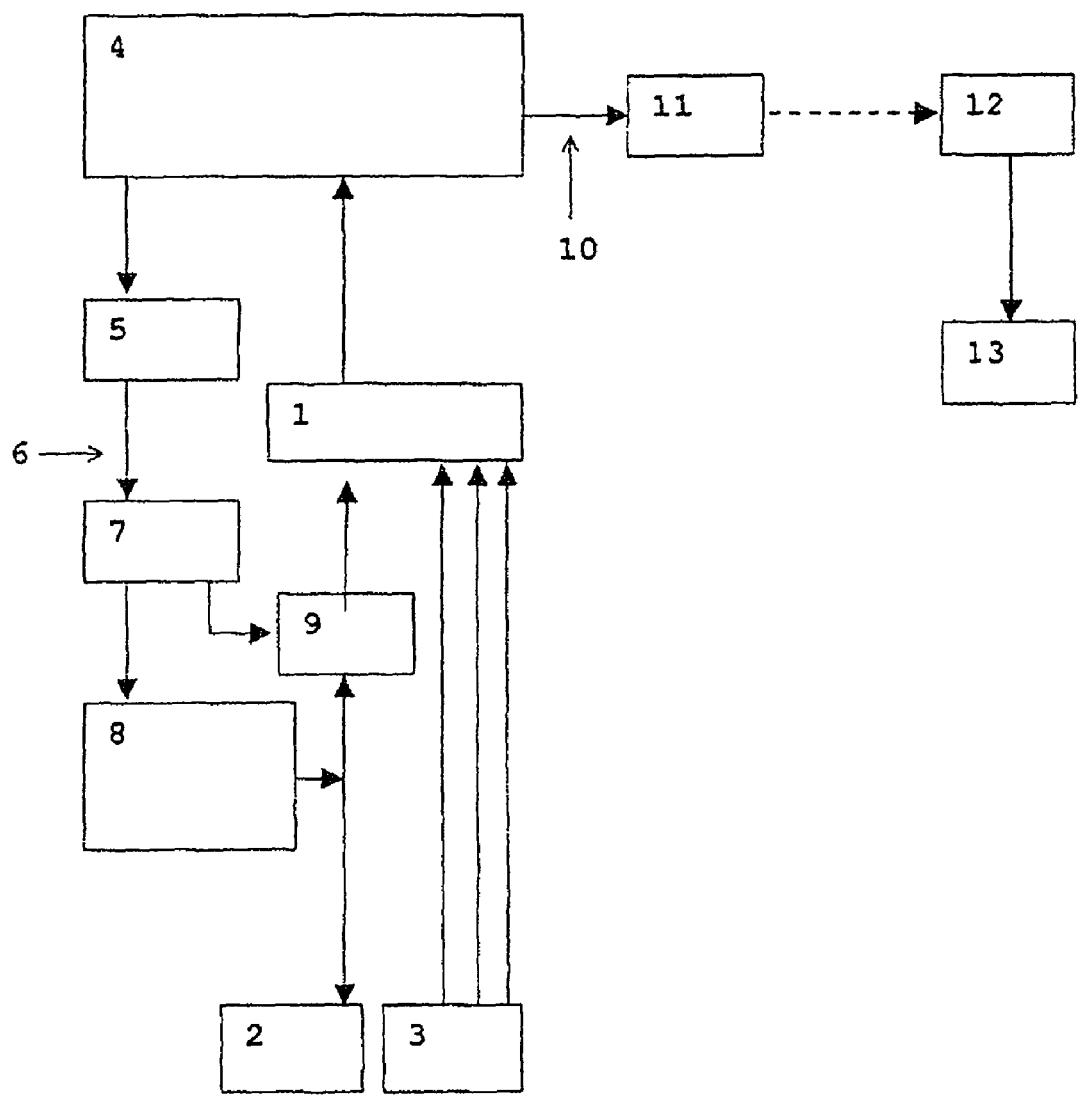
FIG. 1 shows a device according to the invention.
Figure 2:
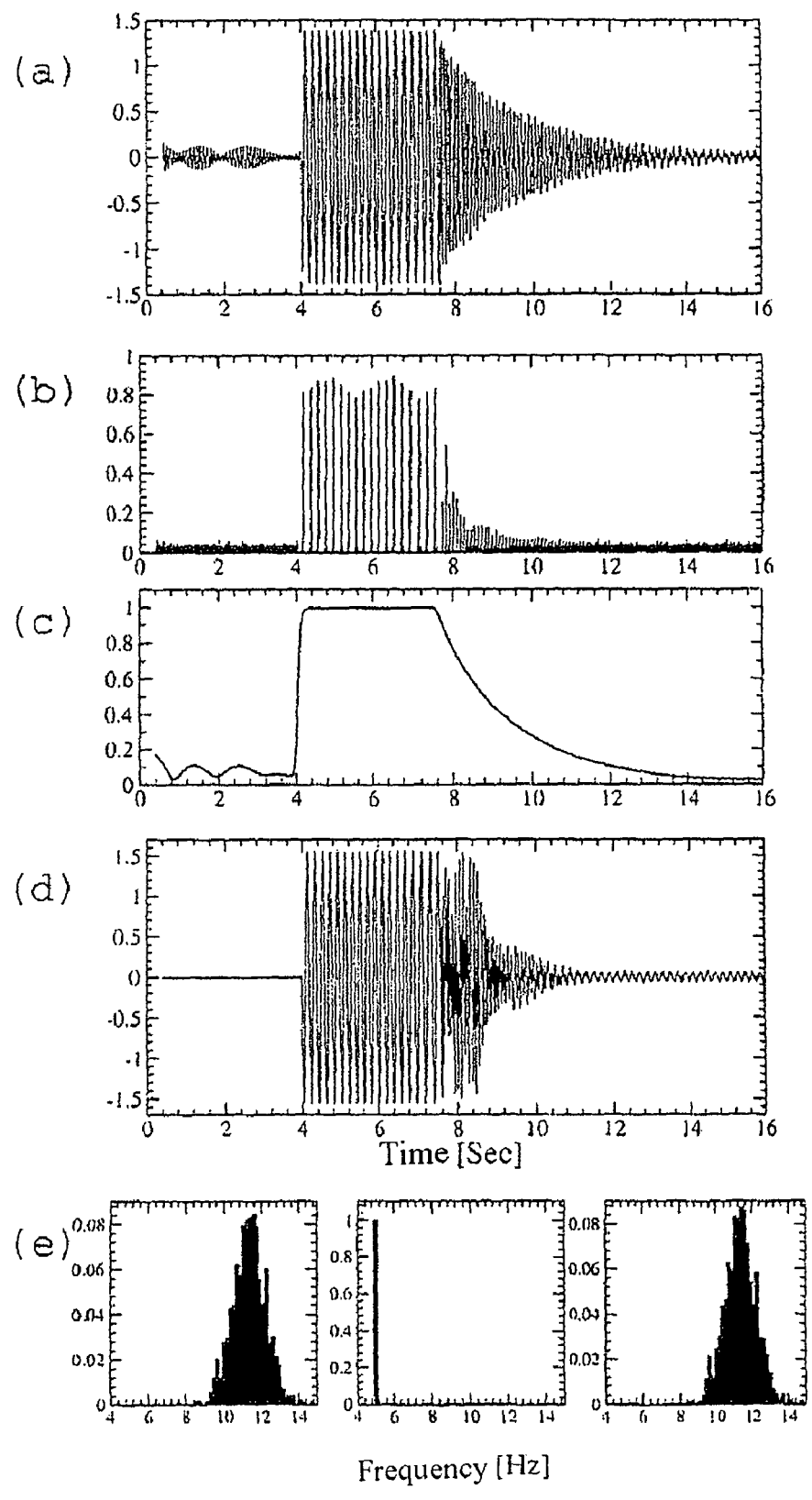
FIG. 2 shows the decoupling effect of stimulation with a stimulation stimulus as described in example 1 in section 8.1. To illustrate, the coupling is switched on at time 4 seconds, stimulation begins at time 7.5 seconds, in FIG. 2a to 2d.
Figure 3:
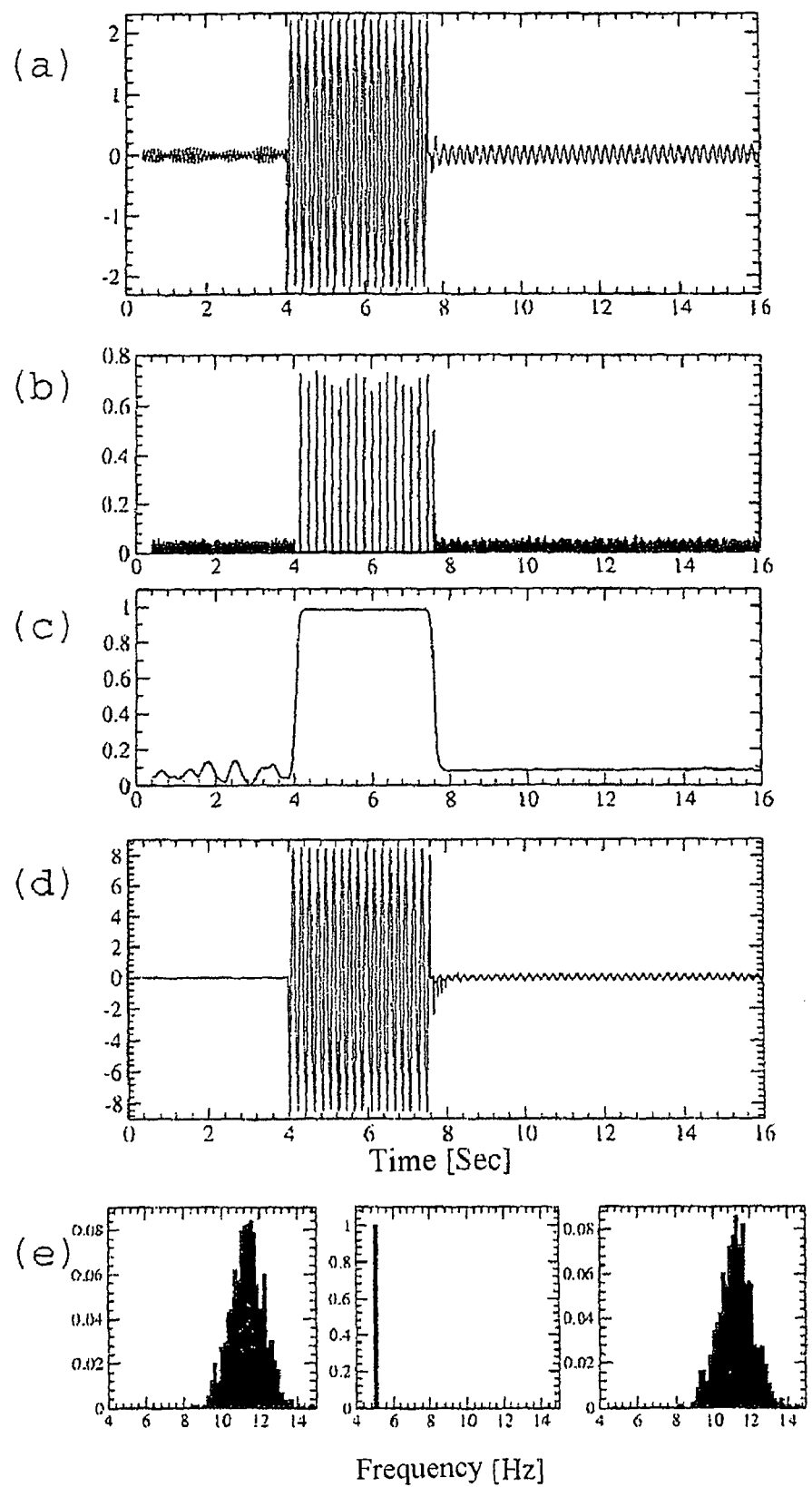
FIG. 3 shows the decoupling effect of stimulation with a stimulation stimulus as described in example 2 in section 8.1. To illustrate, the coupling is switched on at time 4 seconds, the stimulation begins at time 7.5 seconds in FIG. 3a to 3d.

Reference will now be made in detail to the embodiments of the present invention, examples of which are illustrated in the accompanying drawings, wherein like reference numerals refer to the like elements throughout. The embodiments are described below to explain the present invention by referring to the figures.

In FIGS. 2a to d and 3a to d, the abscissa designate the time axes in seconds whereas along the ordinates, the measured neural activity (FIGS. 2a, 3a) or the firing pattern (FIG. 2b, 3*b*) or the extent of synchronization (FIG. 2*c*, 3*c*) or the sum of the coupling and stimulation influences (FIG. 2*d*, 3*d*) are in each case plotted in arbitrary units. The neural activity measured via sensors 3 (FIG. 2*a*, 3*a*) is used as the basis for generating the stimulation stimulus. In FIGS. 2*e* and 3*e*, the abscissa designates the frequency and the ordinates designate the relative number of neurons with the corresponding frequency.

The device according to FIG. 1 comprises an isolating amplifier 1 which is connected to an electrode 2 and at least one sensor 3 for detecting physiological measurement signals. The electrode 2 used can be, for example, an epicortical electrode or brain electrode. The isolating amplifier is also connected to a unit 4 for signal processing and control which is connected to an optical transmitter for the stimulation 5. The optical transmitter 5 is connected via optical waveguides 6 to an optical receiver 7 which is connected to a stimulator unit 8 for signal generation. The stimulator unit 8 for signal generation is connected to an electrode 2. At the input area of the electrode 2 into the isolating amplifier 1, a relay 9 or transistor is located. The unit 4 is connected via a line 10 to a telemetry transmitter 11 which is connected to a telemetry receiver 12 which is located outside the device to be implanted and to which a means for displaying, processing and storing the data 13 is connected. The sensors 3 used can be, for example, epicortical electrodes, brain electrodes or peripheral electrodes.

The electrode 2 can be any electrode which is known to the expert and which is suitable for the application according to the invention. In the wider sense of the invention, an electrode, therefore, is an object which can apply the stimuli according to the invention.

The electrode 2 is, for example, at least two wires to the ends of which a potential difference is applied for the purpose of stimulation. It can be a macro or a microelectrode. As an alternative, the electrode 2 can also be a single wire. In this case, a potential difference is applied between a single wire and the metallic part of the housing of the generator for the purpose of stimulation. Additionally, but not mandatorily, a potential difference can be measured via the electrode 2 in order to register neural activity. In a further embodiment, the electrode 2 can also consist of more than two single wires which can be used both for determining a measurement signal in the brain and for the stimulation.

In the case where the electrode 2 comprises more than two wires, at least one of these wires can also act as sensor 3 so that in this case, an embodiment is present in which in the electrode 2 and the sensor 3 are combined in a single component. The wires of the electrode 2 can have different lengths so that they can penetrate into different brain depths. If the electrode 2 consists of n wires, where n is an integral number of greater than 2, stimulation can be effected via at least one pair of wires, any sub combination of wires being possible in forming the pair. A stimulation can also be performed between one of the n wires and the metallic part of the housing of the generator. Apart from this component, sensors 3 not constructionally combined with the electrode 2 can also be additionally present.

By way of example and illustratively, the neural activity is measured by the device according to the invention in a first step by means of the sensors. In a second step, the stimulation signal is generated by a further processing of the measured signal, e.g. by delaying the neural activity in time and possibly by filtering and/or amplifying it. The stimulation stimulus generated from this stimulation signal is then used for stimulation in a third operating step via an implanted electrode. As a consequence of this stimulation, decoupling and/or desynchronization of the pathological activity occurs in the stimulated tissue. Details of the operation of the device according to the invention are explained in section 1.

As described in section 6, the device according to the invention can be implemented in various embodiments of the temporal control of the stimulus application. The variants of the temporal control of stimulus application are permanent, repetitive and demand-controlled stimulus application.

The permanent stimulus application according to the invention is a simple embodiment of the device according to the invention which operates without additional demand control and applies stimuli permanently as described in section 6.1. The permanent stimulus application thus represents an easily implemented embodiment of the device according to the invention. At the same time, a good decoupling and/or desynchronizing effect of the permanent stimulation occurs due to the self-regulating demand control according to the invention, described in section 5, with little energy input into the population to be decoupled or the population to be desynchronized.

In the repetitive stimulus application according to the invention, the device according to the invention has a control system which is programmed in such a manner that it applies the stimulation stimulus to the electrode 2 only during particular time intervals. There is no stimulation outside these time intervals. The control unit 4 is programmed in such a manner, therefore, that, in the embodiment of the repetitive stimulation described in section 6.2, a stimulation signal is generated with a duration calculated by the control unit 4 at times determined by the control unit 4, for example following one another periodically, and is delivered to the electrode 2. As in the case of permanent stimulus application, the self-regulating demand control of the stimulation signal according to section 5 also occurs in the repetitive stimulus application.

In the demand-controlled stimulus application according to the invention, the device according to the invention has an additional demand control as described in section 6.3. For this purpose, the device according to the invention is preferably equipped with means for detecting the occurrence and/or the instance of the pathological features in the signals of the electrode 2 and/or in the sensors 3 and/or in the neural activity processed. Depending on the occurrence and the instance of pathological features, a stimulus signal is delivered to the electrode 2 in the embodiment of the demand-controlled stimulus application described in section 6.3 so that a stimulation of the brain tissue is effected. By this means, the pathological neural activity in the neuron population is decoupled and/or desynchronized and thus brought closer to the natural physiological state. The pathological activity differs from the healthy activity by a characteristic change in its pattern and/or its amplitude and/or its frequency content and/or in its variation with time. The means for detecting the pathological pattern are a computer which processes the measured signals of the electrode 2 and/or of the sensor 3 and compares them with data stored in the computer. The computer has a data medium which stores data. These can be used as part of the calibration and/or control according to sections 6 and 7. The control unit 4 can comprise, for example, a chip or another electronic device with comparable computing power.

The control unit 4 is programmed in such a manner that, in the embodiment of the demand-controlled stimulus application described in section 6.3, a stimulus is generated and delivered to the electrode 2 in a stimulation interval predetermined by the control unit 4. Overall, all parameters relevant to the respective procedure of the device according to the invention, for the type and intensity of the stimuli and their time delay and information relating to the electrode-related application and also the measurement values relevant for the demand-controlled operation and determined by the sensors 3, or parameters derived therefrom, are to be stored.

The control unit 4 controls the electrode 2 preferably in the following manner: the control data are forwarded by the control unit 4 to an optical transmitter for the stimulation 5, which drives the optical receiver 7 via the optical waveguide 6. The optical coupling of control signals into the optical receiver 7 results in DC isolation of the control unit 4 from the electrode 2. This means that injection of interference signals from the unit for signal processing and control 4 into the electrode 2 is prevented. The optical receiver 7 to be considered is, for example, a photocell. The optical receiver 7 forwards the signals input via the optical transmitter for the stimulation 5 to the stimulator unit 8. Selective stimuli are then forwarded via the stimulator unit 8 to the target area in the brain via the electrode 2. In the case where measurements are also made via the electrode 2, a relay 9 is also driven via the optical receiver 7 from the optical transmitter for the stimulation 5 which prevents interference signals from being injected. The relay 9 or the transistor ensures that the neural activity can be measured again immediately after each stimulus without the isolating amplifier being overdriven. The DC isolation does not mandatorily have to be reproduced by optically coupling in the control signals and, instead, other alternative control systems can be used. These can be, for example, acoustic links, for example in the ultrasonic range. Interference-free control can also be achieved, for example, by using suitable analog or digital filters.

Furthermore, the device according to the invention is preferably connected to means for displaying and processing the measurement and/or stimulation signals and for saving data 13 via the telemetry receiver 12. In this arrangement, the unit 13 can have the methods for data analysis mentioned below.

Furthermore, the device according to the invention can be connected to an additional reference database via the telemetry receiver 13 in order to monitor, for example, the correct operation of the device and possibly make the control mechanisms described in section 7.2 more efficient by modification of the parameters.

In section 1, the mechanism of stimulation is explained in detail. Definitions of the most important terms can be found in section 2. The operating steps from the measurement of the neural activity via their processing up to the generation of the stimulation signal are explained in section 3. The spatial arrangement of the electrode and sensors is the subject matter of section 4. Section 5 deals with the self-regulating demand control of the stimulation signals. In sections 6 and 7, the control of the stimulus application and the calibration and adaptation of the stimulation parameters is described. In section 8, examples and other possible uses and embodiments of the device are explained. The advantages of the device according to the invention are listed in section 9.

1 Mechanism of Stimulation

Figure 4:
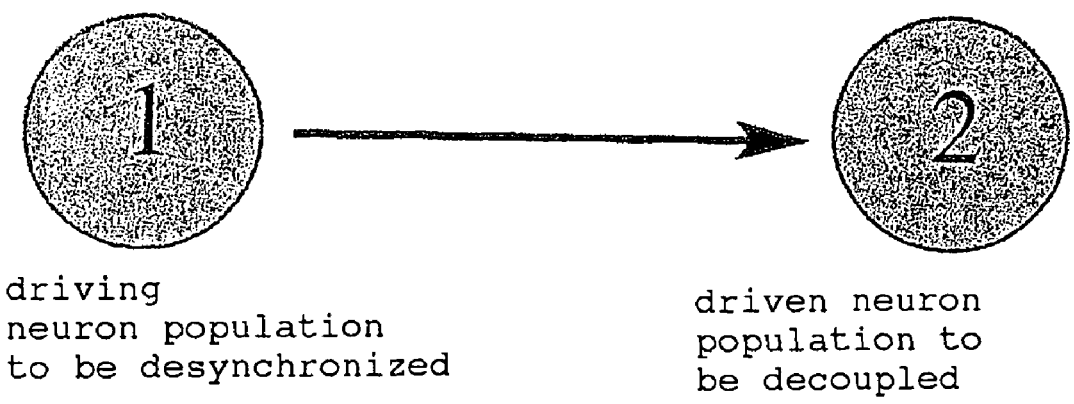
FIG. 4 shows the diagrammatic drawing of the coupling between the driving, pathologically synchronous neuron population 1 and the driven neuron population 2 to be decoupled. For example, neuron population 2 represents the premotor cortex and/or the motor cortex.

The method according to the invention and the device can be used for decoupling the driven neuron population from the driving neuron population. The driving neuron population can also be desynchronized. This relation is shown in FIG. 4.

This is done by applying stimuli by means of an electrode, which are generated by measuring neural activity and, after any processing steps which may exist which preferably also include a time delay, converting it into a stimulation signal and further into a stimulation stimulus and applying it so that a decoupling and/or desynchronization surprisingly occurs. As described in section 3.1, the driven nerve cell population 2 is stimulated in the decoupling procedure (FIG. 4). In the desynchronizing procedure, the driving neuron population 1 is stimulated. Using the device according to the invention and the stimulation method according to the invention, the nerve cell population to be decoupled is directly brought into a decoupled and desynchronized state or the population to be desynchronized is desynchronized. The desired state, that is to say the complete decoupling and/or desynchronization occurs typically during a few periods of the neural activity, frequently in less than one period. The necessity of permanent or repetitive stimulation typically exists since the nerve cell population to be decoupled and/or to be desynchronized, according to experience, resynchronizes again due to the illness and/or due to the coupling, after the stimulation has been switched off. Since, according to the invention, the stimulation is directly associated with the neural activity, the amplitude of the resulting stimulation influence, i.e. the sum of the coupling and stimulation, on the neuron population to be decoupled or to be desynchronized is automatically minimized after successful decoupling and/or desynchronization. This is made possible due to the fact that the feedback stimulation signal, that is to say the processed neural activity, is used as stimulation stimulus, i.e. the extent of synchronization, and thus of the coupling, permanently controls the intensity and form of the stimulation signal. The stimulation signal applied compensates for the force of the external coupling and/or the internal synchronization so that the amplitude of the resultant stimulation influence on the neuron population to be decoupled or to be desynchronized is minimized and their neural activity approaches closer to the natural physiological state. This process works for a large range of modifiable stimulation parameters such as, for example, stimulation period T, the time delay and the intensity, does not need any elaborate calibration and has a large error tolerance. Furthermore, the energy input into the tissue to be decoupled or to be desynchronized is minimized due to the direct relationship between the neural activity and stimulation patterns which allows fewer side effects to be expected.

In the text which follows, the device according to the invention and its operation will be explained by way of example.

The device according to the invention and the control system are equipped with means which can perform all steps of the treatment method according to the invention. With the method steps disclosed, means for carrying out the method step will also be disclosed implicitly. The method steps thus at the same time represent the functionalized device features.

According to the invention, an electrode is introduced into a brain area or—in the case of an epicortical electrode—attached to a brain area. This brain area is preferably selected in such a manner that it is connected directly or indirectly to one or more brain regions or belongs directly to one of these regions which are responsible for forming the disease pattern or are driven by the pathological activity.

In this context, the electrode delivers in its environment an electrical signal which produces a decoupling and/or a desynchronization directly in its environment or in another area conducted away via a nerve fiber bundle. To produce decoupling and/or desynchronization, the neural activity measured and processed, preferably delayed in time, is used as stimulation signal, see section 3. The device according to the invention therefore has a control system which drives the electrode 2 in such a manner that it effects a decoupling and/or a desynchronization in its closer environment and/or in another brain area by forwarding the stimulation via a fiber bundle. According to the invention, the electrode is driven with stimulation stimuli which are formed from the measured and processed neural activity with preferably a time delay of an integral multiple of T/2. T is the stimulation period and essentially approximates, as described below, the period of the rhythmic neural activity of the driving or driven neuron population. If the stimulating electrode 2 is not located in the area to be decoupled and to be desynchronized, the propagation time between the stimulus location and the location of the neuron population influenced by it must be taken into consideration when driving such an electrode 2. This is described in section 7.3. Surprisingly, this stimulation results in a decoupling and desynchronization of the entire neuron population to be decoupled and/or a desynchronization of the neuron population to be desynchronized which is associated with a suppression of the pathological symptoms. If the electrode 2 is located outside the area to be decoupled and to be desynchronized, effects of indirect stimulation must be taken into consideration as described in section 7.3.

Using the novel method and the novel device, the aim of suppressing the pathological symptoms is achieved in a qualitatively different way in comparison with the above-mentioned prior art. Instead of suppressing the neural activity of the pathologically synchronous nerve cell population with a strong stimulation stimulus, the pathologically synchronous driving nerve cell population is simply desynchronized or another neuron population driven by the pathological activity is decoupled from this force and desynchronized which leads to a suppression of the pathological symptoms. The physiological activities of the individual neurons are not influenced. During this process, the neural activity processed according to section 3.3 is used at the location of the stimulus. The decoupling and/or desynchronization occurring surprisingly is supported by the interaction between the neurons in the driven area. This makes use of an active mechanism which is responsible for the pathological synchronization. Illustratively, the energy of the system to be influenced is used for achieving a therapeutic effect with minimum intervention. The best results are obtained if the stimulation stimuli are used which are generated from the stimulation signals whose time delays correspond to the integral multiple of half the stimulation period T. The stimulation period T approximates the period of the pathological activity. However, treatment successes are also achieved if the time delays of the stimuli delivered by the electrode 2 contain other time delays. In such a case, for example, at least a partial decoupling and/or desynchronization is produced. However, the more the time delays selected approach multiples of half the period of the pathological activity, the better will be the treatment results.

2 Definition of Terms

Neural activity:

The description of the mechanism of the device according to the invention is essentially based on the term of neural activity. The neural activity of the neuron population to be decoupled and/or of the neuron population to be desynchronized (see terms of the driving and driven populations) is measured, stored and, according to section 3.3, processed and used as feedback stimulation signal as a result of which the self-regulating demand control according to the invention is implemented. In the text which follows, the measured neural activity of the neuron population to be decoupled and/or of the neuron population to be desynchronized is understood to be a signal which reproduces the development with time of the activity of the neuron population to be decoupled and/or of the neuron population to be desynchronized. For example, local field potential can reproduce the development with time of the activity of the neuron population to be decoupled and/or of the neuron population to be desynchronized. The neural activity can be measured preferably directly in the area to be decoupled and/or in the area to be desynchronized but it is also possible to measure an activity associated with the neural activity of the area to be decoupled and/or of the area to be desynchronized, for example of another brain are*a*, for example of the motor cortex and/or the pre-motor cortex or the activity of a muscle group to be controlled by the area to be decoupled and/or the area to be desynchronized. In a further embodiment of the device according to the invention, neural activities can be measured and combined at various locations in order to obtain an adequate representation of the neural activity of the neuron population to be decoupled and/or of the neuron population to be desynchronized. These quantities associated with the neural activity of the area to be decoupled and/or of the area to be desynchronized will also be called neural activity in the text which follows and are comprised in this term.

Rhythm:

A rhythm is understood to be the rhythmic, that is to say approximately periodic neural activity which can be produced as a consequence of a pathologically excessive synchronous activity of nerve cells. A rhythm can occur for a short time or persist for a long time.

Period:

A central term for the device according to the invention is the period of the rhythmic neural activity which is used as time reference for the application of the stimulation stimuli. Adaptation of the stimulation period T, as described, for example, in section 7.2.1, preferably has the effect that the period of the rhythmic neural activity corresponds to the stimulation period T.

Driving Population:

The driving population is understood to be the nerve cell population which generates the pathologically synchronous neural activity or reproduces the pathologically synchronous activity of a subordinate area. The driving population can forward the pathologically synchronous activity to the driven population (FIG. 4). The pathological rhythm of the driving neuron population is produced (1) with involvement of essentially the entire driving neuron population and/or (2) in a part of the driving neuron population and/or (3) in a third neuron population different from the driving and driven neuron populations, which drives the driving neuron population. In case of (3), the driving neuron population itself is a driven neuron population. The driving neuron population is also called the population to be desynchronized or area to be desynchronized. The driving nerve cell population is not tied to atomical boundaries. Instead, it can also be understood to be at least one component consisting of the group of:

at least one part of at least one anatomical area, at least one complete anatomical area.

Driven Population:

Driven population is understood to be the nerve cell population which is influenced directly or indirectly via the driving population (FIG. 4). Direct influencing means influencing via fibers which connect the two populations directly—i.e. without interposition of another population. Indirect influencing means influencing via at least one interposed population. The nerve cell population which is influenced by the driving population is also called the neuron population to be decoupled or area to be decoupled. The area to be decoupled is not tied to anatomical boundaries. Instead, it can also be understood to be at least one component consisting of the group of:

at least a part of at least one anatomical area, at least one complete anatomical area.

The connection of the areas of nucleus subthalamicus—globus pallidus exterior, which, due to the disease, act as pacemakers and can generate a pathologically rhythmic synchronous activity, can be used as an example of a driving neuron population. The synchronous activity generated controls the neural activity of the cerebrum area, e.g. of the motor cortex which can here be called the driven population and is also connected to muscles and controls their activity.

Decoupling Stimulation:

A decoupling stimulation in the sense of the invention is understood to be a stimulation which minimizes the pathologically driving effect of the driving neuron population on the driven neuron population to such an extent that it no longer plays a role functionally—that is to say for the instancing of the symptoms.

Target Population:

In the text which follows, the target population is understood to be the nerve cell population stimulated directly by an implanted stimulation electrode. A target population is stimulated directly by an electrode implanted in it or close to it. The populations to be decoupled and/or to be desynchronized are stimulated either directly or indirectly.

Direct Stimulation:

In this case, the stimulation electrode 2 is located directly in the area to be decoupled or in the area to be desynchronized. This electrode 2 influences the target population which is located in the area to be decoupled or in the area to be desynchronized.

Indirect Stimulation:

In this case, the area to be decoupled or the area to be desynchronized is not stimulated directly by means of the stimulation electrode 2. Instead, a target population or a fiber bundle which is functionally closely connected to the area to be decoupled or the area to be desynchronized is stimulated by the electrode 2. In this process, the stimulation effect on the area to be decoupled or the area to be desynchronized is conducted away preferably via anatomical connections. For the indirect stimulation, the term target area will be introduced as generic term for target population and fiber bundle. Of the term target area, the neuron population functionally closely connected to the area to be decoupled or the area to be desynchronized, and the connecting fiber bundle are to be understood in the text which follows which are stimulated directly by the implanted electrode 2.

Time Delay:

The device according to the invention forwards signals to the stimulation electrode 2 which, according to section 3.2, can correspond to measured and possibly processed neural activity (=feedback stimulation signal) at an earlier time. This time shift will be called time delay in the text which follows and represents an important stimulation parameter associated with the stimulation period T, which corresponds to the period of rhythmic neural activity.

Feedback Stimulation Signal:

Feedback stimulation signal or stimulation signal is understood to be the signal which represents the measured and processed neural activity and is used as basis for the stimulation stimuli. The processing steps can be carried out, for example, as described in section 3.3. The stimulation signal is composed of the processed neural activity and used for stimulating the brain area to be decoupled or the brain area to be desynchronized. Performing the feedback stimulation signal, it may be necessary to generate measurement signals by multiple processing steps, which are possibly independent of one another, with different processing parameters (particularly different time delays) which are then e.g. added and/or multiplied and/or divided and/or subtracted and/or calculated by means of other nonlinear functions, for forming the actual stimulation signal. From the feedback stimulation signals, stimulation stimuli are generated and then applied to the target population by means of the electrode.

Resultant Stimulation Influence

The resultant stimulation influence on the neuron populations to be decoupled or the neuron populations to be desynchronized is understood to be the sum of the external forces applied to the population to be decoupled and/or to be desynchronized. According to section 3.1, in one embodiment of the device according to the invention, the driven neuron population is decoupled from the driving neuron population by means of direct or indirect stimulation. In this case, the resultant stimulation influence on the population to be decoupled is the sum of the stimulation signal and of the driving force of the coupling to the driving population. In another embodiment of the device according to the invention, the driving population to be desynchronized is desynchronized by means of the stimulation. The resultant stimulation influence on the population to be desynchronized is here only the stimulation signal. Due to the self-regulating demand control described in section 5, the amplitude of the resultant stimulation influence on the neuron population to be decoupled or the neuron population to be desynchronized is automatically minimized after successful decoupling and/or desynchronization.

3 Stimulation Method and Form of Stimulus 3.1 Decoupling and Desynchronizing Method A pathologically synchronous neuron population in a brain area can act as driving force on another following neuron population due to rhythmic activity. This can result in an interaction scheme in the form of "driving population—driven population" between the populations as is shown diagrammatically in FIG. 4. If the driving force is strong enough, the driven neuron population will also become synchronized which can produce the pathological symptoms. This occurs when the driven population drives the muscles as is the case in the premotor cortex or motor cortex.

As described in section 1, it is the aim of the device according to the invention and of the stimulation methods according to the invention to desynchronize the pathologically synchronous neural activity which allows the suppression of the symptoms to be expected. In the case of the decoupling stimulation mode, the driven neuron population 2 is decoupled from the driving population 1, and desynchronized, or, in the case of the desynchronizing stimulation mode, the driving neuron population 1 is desynchronized, for this purpose.

In the decoupling stimulation mode, the driven neuron population 2 is stimulated directly or indirectly according to sections 3.4 and 4.1 by means of a stimulation electrode. The stimulation produces a decoupling of the neuron population from the driving neuron population 1 which results in a desynchronization of the population 2.

In the desynchronizing stimulation mode, the driving neuron population 1 is stimulated directly or indirectly by means of a stimulation electrode. By means of this stimulation, population 1 is desynchronized so that its driving force on the population 2 disappears. The latter is also desynchronized as a result of which the pathological symptoms are suppressed. If population 2 synchronizes itself, it must be desynchronized directly like a driving neuron population.

According to section 5, a self-regulating demand control of the stimulation signal occurs in the two above-mentioned stimulation methods, wherein the resultant stimulation influence on the stimulated neuron population is automatically minimized. According to section 2, the resultant stimulation influence on the driven neuron population in the decoupling stimulation mode is the sum of the stimulation signal and of the driving force of the driving population. In the desynchronizing stimulation method, the resultant stimulation influence on the driving neuron population is exclusively the influence of the stimulation signal.

In the text which follows, an embodiment of the device according to the invention is described by way of example, namely the decoupling stimulation mode in which the neuron population to be decoupled is decoupled from the driving neuron population by means of direct or indirect stimulation. The further embodiments of the device according to the invention are described in section 8.

3.2 Measuring the Neural Activity

The variation with time of the neural activity of the area to be decoupled and/or of the driving area can be measured directly and/or indirectly via the sensors 3.

In the case of an indirect measurement, the variation with time of the activity of a muscle group influenced by the area to be decoupled and/or of the driving area and/or the variation with time of the activity of a neuron population associated with the area to be decoupled and/or the driving area is measured.

The sensors 3 (see FIG. 1) are located in the brain and/or outside the brain. In the brain, they are positioned in the area to be decoupled and/or the driving area and/or in at least one other area functionally connected thereto. Outside the brain, the sensors 3 are located on body parts which are connected to the pathologically synchronized neural activity, e.g. as electrodes in a trembling muscle. The measured signals of the neural activity of the neuron populations, for example of the muscular activity (which is also called neural activity, see section 2) are processed and stored in a unit for signal processing 4. The measuring, processing and storing can be carried out permanently or at discrete time intervals. In the latter case, the duration and/or the intervals of the discrete measuring intervals are determined by a deterministic and/or stochastic algorithm.

3.3 Processing the Neural Measurement Signals

The measurement signals stored in the unit for signal processing 4 are then processed in order to be available as feedback stimulation signals. The following processing steps can be applied:

1. The measured neural activity can be filtered, e.g. the neural activity can be band-pass filtered. The filtering may be necessary if, apart from the disease-related activity, non-disease-related activity is measured via sensor 3, for example from other neuron populations. Since the disease-related activity typically occurs in a frequency range which differs from the frequency range of the non-disease-related activity, the activity is preferably determined in the disease-related frequency range in this case. This is achieved, for example, by means of a frequency analysis. Similarly, it may be necessary to perform a wavelet analysis and/or a Hilbert transformation and/or filtering in the time domain.

2. If the neural activity of the neuron population to be decoupled and/or of the neuron population to be desynchronized is measured via a number of sensors 3, the measured neural activities can be combined linearly and/or nonlinearly. For example, the measured neural signals are multiplied, divided, added and/or subtracted with one another or with themselves and/or transformed by means of other nonlinear functions.

3. The measured neural activity is delayed in time. The time delays used for this purpose are defined in section 3.4 and also take into consideration the position of the stimulation electrode with respect to the neuron population to be decoupled, according to section 7.3. In addition, the time delays can be adapted preferably during the stimulation according to section 7.2.1 and 7.2.2.

4. The measured neural activity is amplified. The measured neural activity is typically less by a few orders of magnitude than the stimulation amplitudes which, according to experience, lead to a stimulation effect. For this reason, amplification must be carried out which can be adapted during the stimulation according to section 7.2.3.

5. The measured neural activity is time-coded. Since signals with large gradients have a great effect on the neural dynamics, the measured neural activity is coded, for example, in the form of pulse trains or low- or high-frequency pulse trains consisting of short rectangular pulses. To enhance the effect of the stimulation, other coding methods can also be used.

6. The polarity of the neural activity is changed.

7. The neural activity is transformed linearly and/or nonlinearly. This can be done, e.g. with the aid of the Hilbert and/or Fourier and/or wavelet transformation.

8. The maximum amplitude of the stimulation signal is limited.

9. The measured neural activity is transformed in such a way that stimulation signals are produced whose net charge input is essentially zero.

10. The measured neural activity is used directly as feedback stimulation signal.

The processed neural activity, i.e. the feedback stimulation signal, is determined by applying at least one component of the above-mentioned processing steps.

For example, the stimulation signals can be generated from the measured neural activity using always the same processing steps. As well, the set of treatment steps and/or their parameters can be varied in time by a deterministic and/or stochastic and/or combined stochastic/deterministic algorithm.

3.4 Form of the Stimulation Stimulus

A stimulation stimulus is understood to be a stimulus which is applied via the electrode 2 and acts in a time interval. To form a stimulation stimulus, the feedback stimulation signals, that is to say the neural activity processed according to section 3.3, are used. To generate stimulation stimuli, the stimulation signals are, for example, multiplied, divided, added and/or subtracted with one another and/or with themselves and/or transformed by means of other nonlinear functions.

The time delays used during the processing of the neural activity are specified, for example, as fractions of the period of the oscillatory neural activity to be decoupled and/or driving neural activity and are preferably essentially a multiple of one Nth of the period, where N is a small integral number, for example 2. The time delays of the stimulation signals can also be selected, e.g., to be greater than the stimulation period T. The device according to the invention also provides the possibility of using a number of preferably different time delays for forming the stimulation stimulus. The resultant time-delayed feedback stimulation signals can be combined linearly and/or nonlinearly to form a stimulation stimulus.

For this purpose, the device according to the invention has means which apply the electrical stimulation stimulus described in the manner described. The means are the electrode 2, a control system 4 which delivers control signals to the electrode 2 for delivering these stimuli. Furthermore sensors 3 and the unit for signal processing 4 which receives the neural activity and prepares it for further use as stimulation stimulus. A stimulation stimulus is preferably generated, the net charge input of which is essentially zero.

For example, the electrode 2 can be driven with the same stimulation stimulus in the form of the same processed neural activity according to section 3.3. The electrode 2 can also be driven with different stimulation signals and/or combinations of the stimulation signals and/or by means of different transformations and/or combinations of the stimulation signals.

The order and/or the type and/or the energy input and/or the parameters of stimuli can be determined by means of a deterministic and/or stochastic and/or combined stochastic/deterministic algorithm.

The time delays and/or polarity and/or application period and/or intensity of the stimulation stimulus, used in the processing steps, see section 3.3, can be varied systematically or randomly controlled, that is to say in accordance with a deterministic or stochastic rule. For this purpose, the device according to the invention has a control system which is programmed in such a manner that it deterministically and/or stochastically activates the time delays and/or the polarity and/or the application period and/or the intensity of the processing steps of the stimulation stimulus.

By varying the time delays and/or the polarity and/or the application period and/or the intensity within the processing steps of the stimulation signal, adaptation processes in the neuron populations which produce an increase in the stimulation intensity in order to achieve the same therapeutic effect, can be prevented.

4 Spatial Arrangement of the Electrode and Sensors 4.1 Stimulation Electrode

An electrode 2 is preferably used for the stimulation.

In the case where the electrode 2 is positioned in the nerve cell population to be decoupled, the electrode should be arranged preferably in such a manner that the electrode can be used for stimulating the entire nerve cell population to be decoupled. This can be achieved by geometric positioning of the electrode. For example, the electrode 2 can be positioned in the center of the area to be decoupled.

In the case where the electrode 2 is not positioned in the nerve cell population to be decoupled, stimulation is applied in a target area which differs from the area to be decoupled in this form of stimulation. The indirect stimulation can then be applied by stimulation of a neuron population which differs from the nerve cell population to be decoupled and/or by stimulating a fiber bundle connected to the nerve cell population to be decoupled.

4.2 Number of Sensors

The mechanism of the device according to the invention essentially consists in that, as described in section 1 and 3, the measured and processed neural activities of the neuron population to be decoupled and/or of the driving neuron population are applied again as stimulation. The sensors 3 are one of the most important components of the device according to the invention and can be positioned either outside the neuron population to be decoupled and the driving neuron population or preferably directly in the neuron population to be decoupled and/or the driving neuron population, as described in section 3.2. Only one sensor 3 is preferably used for detecting the activity of the neuron population to be decoupled and/or of the driving neuron population. As a result, the number of sensors to be implanted is kept as small as possible in order to prevent unnecessary tissue damage and, especially, brain bleeding during the implantation. However, two or more sensors can also be used, for example, in order to reconstruct the neural activity of the neuron population to be decoupled and/or of the driving neuron population much more completely as combination of the measured activities.

Furthermore, possible brain damage caused by the implantation is reduced further or avoided, and the stimulation effect is improved, by combining at least one sensor 3 and stimulation electrode 2 in one electrode to be implanted.

In the case where the sensors 3 are all positioned in the nerve cell population to be decoupled and/or the driving nerve cell population, the sensors 3 should be arranged preferably in such a manner that a large proportion of the nerve cell population to be decoupled and/or of the driving nerve cell population can be covered by means of the sensors. This can be achieved with a geometric arrangement of the sensors with regard to the tissue to be decoupled and/or the driving tissue. In the case of arrangement with only one sensor 3, the latter can be located, for example, in the center of the tissue. In the case of arrangements with a number of sensors, the sensors can be arranged, for example, in a symmetric manner. In the case where at least one of the sensors 3 is not positioned in the nerve cell population to be decoupled and the driving nerve cell population, an activity associated with the neural activity of the neuron population to be decoupled and/or the driving neuron population is measured in at least one area different from the area to be decoupled and the driving area in this form of activity measurement. As described in section 3.2, the indirect measurement can be effected by measuring the activity of a neuron population different from the nerve cell population to be decoupled and the driving nerve cell population and/or of a fiber bundle and/or of a body part which is connected to the nerve cell population to be decoupled/the driving nerve cell population.

5 Self-Regulating Demand Control of the Stimulation Signal

One of the most important characteristics of the mechanism of the device according to the invention is a self-regulating demand control of the stimulation signal. The self regulation described occurs due to the fact that the stimulation stimuli consist of the neural activity processed. In the case of a more intensive synchronous activity in the area to be decoupled and/or of a coupling with the driving population of the area to be decoupled, a great variance of the measured neural activity must be expected as is known to the expert. This leads directly to a stimulation, time delayed in accordance with the invention, with increased stimulation amplitude. According to the invention, and illustratively, the force of the applied stimulation signal compensates for the force of the internal synchronization and/or the coupling with the driving population of the area to be decoupled, resulting in decoupling and desynchronization of the population to be decoupled. As a result, the amplitude of the resultant stimulation influence on the population to be decoupled, i.e. the sum of the stimulation and coupling, is independently minimized. After decoupling and desynchronization has been achieved, a neural activity of little variance is expected as a result of which the stimulation signals are influenced directly and are independently adapted. If a new coupling and/or resynchronization again occurs, the device according to the invention automatically takes into account the increased demand for decoupling and/or desynchronizing stimulation in that the greater variance of the neural activity leads to a stronger stimulation stimulus being formed. This represents a self-regulating demand control of the device according to the invention.

The mechanism forming the basis of the self-regulating demand control acts in all embodiments of the device according to the invention, described in greater detail in the text which follows.

6 Control of the Stimulus Application

The temporal control of the stimulus application is understood to be an embodiment of the device according to the invention which is preferably programmed in advance, the stimulation stimulus being applied in a particular way by means of the stimulator unit 8. The variants of the temporal control of the stimulus application are permanent, repetitive and demand-controlled stimulation application. In addition, a manual demand control can be implemented, for example for a stimulus application carried out by the patient or the doctor.

6.1 Permanent Stimulus Application

In the permanent stimulus application, the device according to the invention has a control system which is programmed in such a manner that it performs a continuous application of the stimulation stimulus at the electrode 2. The permanent stimulus application represents the simplest, and easily implemented embodiment of the device according to the invention. At the same time, the permanent stimulation produces a good decoupling and desynchronizing effect with little energy input into the population to be decoupled due to the self-regulating demand control according to the invention, described in section 5.

During the permanent stimulus application, the intensity parameters can be adapted in accordance with section 7.2.3. Similarly, the time parameters—stimulation period T and/or time delay—can be adapted during the permanent stimulation in accordance with section 7.2.1 and 7.2.2 in combination with an adaptation of the stimulation intensity or independently thereof.

6.2 Repetitive Stimulus Application

In the repetitive stimulus application, the device according to the invention has a control system which is programmed in such a manner that it performs an application of the stimulation stimulus at the electrode 2 only during particular time intervals. There is no stimulation outside these time intervals.

In the repetitive stimulus application, the stimulation stimulus can be imparted strictly periodically in time or non-periodically in time. In this embodiment, the device according to the invention has a control system which is programmed in such a manner that it controls the time intervals between the stimulation intervals and/or the duration of the intervals periodically and/or non-periodically. A temporally non-periodic sequence of the stimulation stimulus can be generated by a stochastic and/or deterministic and/or combined stochastic/deterministic algorithm in order to achieve the desired decoupled and desynchronized state of the population to be decoupled. Analogously, in the text which follows, a combination of deterministic and stochastic rules is understood to be a functional relationship in which deterministic and stochastic terms are functionally linked to one another, e.g. by addition and/or multiplication.

The stimulation and measuring intervals can be arranged to overlap or to occur at the same time or separated in time. During the repetitive stimulus application, the intensity parameters can be adapted according to section 7.2.3. Similarly, the time parameters—stimulation period T and/or time delays—can be adapted during the repetitive stimulation according to section 7.2.1 and 7.2.2, in combination with an adaptation of the stimulation intensity or independently thereof.

6.3 Demand-Controlled Stimulus Application

In the demand-controlled stimulus application, the device according to the invention has a control system which is programmed in such a manner that it performs the switching-on and -off of the stimulation stimulus in accordance with the particular states of the neuron population to be decoupled and/or the driving neuron population. For this purpose, the control unit 4 uses the measurement signals and/or the stimulation signals for detecting a pathological feature. The stimulation is switched on, for example as described in the text which follows.

The activity of the neuron population to be decoupled and/or of the driving population is measured via the sensor 3. The neural activity is forwarded to the unit 4 for signal processing and/or control which, among other things, acts as means for detecting a pathological feature. As soon as the unit 4 for signal processing and/or control detects a pathological feature in the neural activity, the application of a stimulation stimulus is started. As soon as the pathological feature disappears due to the effect of the stimulation applied, the stimulation is preferably switched off. The device according to the invention therefore comprises in one possible embodiment as unit 4 for signal processing and/or control, a computer which contains a data medium which carries the data of the disease pattern and compares it with the measurement data. Data of the disease pattern are understood to be parameters and measurement variables of relevance to the stimulation, for example the instantaneous frequency of the neural activity measured via the sensor 3, of the threshold value necessary for the procedure of the demand-controlled stimulus application, the stimulation parameters which specify the stimulus intensity. A pathological feature is understood to be, for example, a disease-related synchronization of the neuron population to be decoupled/of the driving neuron population and can be recognized by the following characteristics of the neural activity:

a) If via the sensor 3, it is exclusively or predominantly the pathological activity of the neuron population to be decoupled and/or of the driving neuron population which is measured as, e.g. in the direct measurement described in section 3.2 and section 4.2, the neural activity is used directly for determining whether the amplitude of the neural activity exceeds a threshold value. In a preferred embodiment, the device according to the invention is therefore equipped with means for detecting a value of the amplitude of the neural activity which corresponds to the threshold value. In this case, the neural activity itself and/or its amount and/or its amplitude is preferably compared with the threshold value. In this embodiment, the means for detecting the threshold value can be programmed in such a manner that it compares, for example, the neural activity itself and/or its amount and/or its amplitude with the threshold value.

The amplitude is determined either in a simple version by determining the amount of the signal and/or with band-pass filtering and/or Hilbert transformation and/or wavelet analysis. In this case, the unit 4 for signal processing is programmed in such a manner that it can perform a determination of the amount of the signal and/or band-pass filtering and/or Hilbert transformation and/or a wavelet analysis. The neural activity or its amount is especially preferably used since the calculation of the amplitude means a distinctly higher computational effort and the amplitude cannot be determined on a single measurement value of the neural activity but must be determined in a sufficiently large time interval known to the expert which can slightly delay the detection of the pathological feature.

b) If, in addition to this pathological activity of the neuron population to be decoupled and/or the driving neuron population, non-disease-specific activity is additionally measured via the sensor 3, for example from other neuron populations as, e.g. in the indirect measurement described in sections 3.2 and 4.2, a further algorithmic step must be inserted in the analysis of the neural activity. Since the disease-specific activity occurs typically in a frequency range which differs from the frequency range of the non-disease-specific activity, it is sufficient for this purpose to preferably perform an estimation of the activity in the disease-specific frequency range. The frequency of the disease-specific activity is determined, for example, by determining the difference of successive trigger points. Trigger points are points such as maxima, minima, turning points and zero transitions. This analysis is preferably performed in a sliding time window, forming the mean value of a number of temporal differences which increases the stability. As an alternative, the frequency can also be estimated with the spectral estimating methods known to the expert and other frequency estimators such as, e.g. with the aid of a Fourier analysis. For this purpose, the device according to the invention, in a particular embodiment, has means for estimating the activity in the disease-specific frequency range such as spectral estimating methods, Fourier and/or wavelet analysis etc. This is implemented, for example, by means for performing a frequency analysis. For example, the spectral energy in the disease-specific frequency range can be determined in a sliding window. As an alternative, the amplitude in the disease-specific frequency range can be determined, after band-pass filtering, by determining the maximum of the band-pass-filtered signal or by determining the mean value of the amount of the band-pass-filtered signal and/or by Hilbert transformation and/or by wavelet analysis. For this purpose, the device according to the invention has, for example, means for band-pass filtering the amplitude and means for determining the maximum of the band-pass filtered signal and/or means for determining the mean value of the amount of the band-pass filtered signal and/or means for performing a Hilbert transformation and/or a wavelet analysis.

In the case of demand-controlled stimulus application, the same stimulation stimulus is always used, for example. The stimulation period T is preferably adapted, as described in section 7.2.1 to the instantaneous frequency of the neuron population to be decoupled and/or of the neuron population to be driven. When the pathological feature is present, a stimulus is then applied with a stimulation period T adapted to the instantaneous frequency. Similarly, the time delays can be adapted according to section 7.2.2 and/or the intensity of this stimulus remains preferably constant. However, the intensity parameters can also be modified in accordance with the stimulation effect as in section 7.2.3.

6.3.1 Determining the Demand

There are at least two reasons why there is no unambiguous relation between the instance of the pathological feature and the instance of the disease-specific symptoms. On the one hand, the distance of the sensor 3 from the area to be decoupled and/or the driving area in which the neural activity to be measured is generated results in a change in the amplitude in the disease-specific frequency range. On the other hand, a particular instance of the disease-specific feature, that is to say the instance of the rhythmic activity in the disease-specific frequency range, is not unambiguously associated with the disease-specific symptoms. Since the disease-specific rhythm has effects on complex neural networks in the brain which, in addition, typically do not obey simple linear dynamic rules, there are no unambiguous relations between disease-specific rhythm and the instance of symptoms. If, for example, the disease-specific rhythm does not sufficiently correspond to the biomechanically determined natural frequency of an extremity, the tremor caused by the disease-specific rhythm is distinctly less than if the disease-specific rhythm resonates with the biomechanically predetermined natural frequency of the extremity.

The characteristics such as, e.g. the dominant frequency and the amplitude of the measured neural activity lie in a range of experience known to the expert. The value of the instance of the disease-specific feature of the neural activity measured via sensor 3 is called the threshold, the transgression of which typically gives rise to the occurrence of symptoms, for example of the tremor. The threshold is a parameter which must be selected for the embodiment of the demand-controlled stimulus application described in section 6.3. The device according to the invention, therefore, comprises means for detecting a threshold value in the form of the control unit 4. The method of demand-controlled stimulus application according to the invention achieves the advantage that the effectiveness of the device according to the invention does not critically depend on the choice of threshold but a large error tolerance with respect to the choice of threshold is given which lies, for example, within a range of up to 50% of the maximum instance of the disease-specific feature. The choice of threshold is determined either intraoperatively or preferably in the first case after the operation by measuring the neural activity via sensor 3 with determination of the instance of the disease-specific feature and comparison with the instance of the symptoms, e.g. the intensity of the trembling.

In a less preferred embodiment of the demand-controlled stimulus application, the threshold is taken to be a representative value, for example the mean value of a collective of threshold values measured in patients. In a preferred embodiment, the choice of threshold is checked in essentially regular intervals, for example during half-yearly controls.

In the embodiments of the permanent and repetitive stimulation with demand-controlled stimulus intensity, described in sections 6.1 and 6.2, no threshold value detection is necessary.

The three stimulation methods described above can be used preferably in different combination with the methods for adapting the stimulation parameters, described in section 7.2.

All three stimulation methods have in common the inherent self-regulating demand control according to the invention. The direct dependence of the stimulation signal on the neural activity measured necessitates a self-regulating demand control, described in section 5, as a result of which the energy input into the population to be decoupled is minimized. This self-regulating demand control acts independently of the implementation of the additional demand control described in section 6.3 and of the calibration and control of the parameters as described in section 7.

7 Calibration and Adaptation of the Parameters

In the text which follows, it is assumed that the electrode 2 is located in the neuron population to be decoupled. The case where the electrode is located outside the neuron population to be decoupled is considered separately at the end of the section. A calibration and adaptation can be performed for the following parameters of the device according to the invention, for example: the frequency of the stimulation signals, the reciprocal of which corresponds to the stimulation period, the time delays of the stimulation signals and the intensity of the stimulation stimulus.

7.1 Stimulation Parameters at the Beginning of the Stimulation

7.1.1 Frequency, Stimulation Period

Choice of frequency without previous operation of the device: the frequency range of the pathological neural activity is known to the expert for the respective disease patterns (Elble R. J. and Koller W. C. (1990): Tremor, John Hopkins University Press, Baltimore). Of this frequency range, the mean value can be preferably taken. As an alternative, the value of the frequency to be expected in relation to age and sex can be used instead.

For a successful operation of the device according to the invention, it is not necessary that the frequency initially predetermined corresponds to the frequency of the activity of the neuron population to be decoupled or of the activity of the driving neuron population, actually present. The control of the stimulation period T described at 7.2.1 functions even when an initial value is used which deviates greatly from the correct frequency value. Deviates greatly means that the value can also be too large or too small by a factor of at least 10. As an alternative, it is thus also possible to preferably begin with a frequency value which lies within the frequency range typical of the disease and known to the expert. The value of the frequency at the beginning of the stimulation can also be preferably obtained by individual adaptation to the respective patient. This can be achieved, for example, by a measurement of the neural activity and estimation of the dominant frequency of the activity of the neuron population to be decoupled and/or the driving neuron population as described in section 6.3, in preparation for the stimulation.

Choice of frequency with previous operation of the device: the starting value for the frequency is selected to be the mean value of the frequency during the preceding operation of the device.

In both cases, that is to say with and without previous operation of the device, the stimulation period T is calculated as the reciprocal of the starting value of the frequency.

7.1.2 Time Delays

The time delays of the stimulation signals are preferably determined after a first determination of the stimulation frequency or of the stimulation period T, respectively. The time delays are preferably selected as fractions of the stimulation period T, e.g. T/2. Preferably, time delays can also be selected which correspond to a multiple of fractions of the stimulation period T and possibly exceed the stimulation period T. The adaptation of the time delays described in section 7.2.2 also works in the case described above in which at least some of the time delays of the feedback stimulation signals from which the stimulation stimuli are generated are different and/or exceed the stimulation period T.

7.1.3 Intensity

The starting values of the stimulation parameters which determine the intensity of the stimulation stimulus (e.g. amplification of the feedback stimulation signal) are determined in accordance with the experimental values known to the expert (e.g. maximum amplitude 10 V). The control of the intensity described at 7.2.3 also works if a starting value is used which greatly differs from the most advantageous intensity value. Differs greatly means that the value can also be too large by at least a factor of 10 (preferably maximum amplitude 10 V) or too small. As an alternative, it is thus also possible to preferably begin with an intensity value which lies within the range known to the expert. In particular, it is preferred to begin a stimulation with small values of intensity, for example maximum amplitude of 0.5 V, of the stimulation signal in order to thus possibly reduce the side effects of the stimulation. If there is a necessity to use a stronger stimulation signal, the intensity can be increased in small steps as described in section 7.2.3.

The starting values for frequency and intensity can thus be predetermined and, in particular, do not need to be determined as part of a time consuming calibration.

7.2 Adaptation of the Stimulation Parameters

7.2.1 Adaptation of the Stimulation Period T

In the area to be decoupled and/or in the driving area and/or an area functionally closely connected thereto, the neural activity is measured which, after processing, is used as stimulation signal. For example, in Parkinson's disease, apart from a measurement via the sensors 3 directly in the area to be decoupled and/or in the driving area, the activity can also be measured in a following area, e.g. the premotor cortex via epicortical sensors. In a time window with a length specified below, the dominant mean period is determined. For this purpose, different algorithms can be used. For example, the stimulation period T can be adapted to the instantaneous period of the neuron population to be decoupled and/or the driving neuron population. For example, the instantaneous period can be determined as the time difference between two successive maxima of the measured neural activity. As well, for example, the mean frequency of the neural activity can be estimated first and the stimulation period T can be determined as reciprocal of the mean frequency. If not only disease-specific activity is measured via the sensor 3, the disease-specific activity must first be extracted via band-pass filtering of the frequency range specific to the disease for this type of frequency estimation. As an alternative, for example, the frequency can be determined via the frequency estimators mentioned in section 6.3. The time window used for this frequency estimation has a length which can be open towards upper values and corresponds to, for example 10000 periods, preferably 1000 periods, particularly preferably 100 periods of the pathological activity, but also to other arbitrary values.

7.2.2 Adaptation of the Time Delays

As described in sections 3.4 and 7.1.2, the time delays of the stimulation signals are preferably selected as fractions of the stimulation period T. During the stimulation, the time delays can be fixed, for example, or preferably adapted to the stimulation period adapted in accordance with section 7.2.1. To be able to achieve an optimum decoupling and/or desynchronization with little resultant stimulation influence, the time delays of the stimulation signals are varied preferably during the stimulation by a deterministic or stochastic and/or combined stochastic/deterministic algorithm. For this purpose, the device according to the invention comprises means in the form of the control unit 4 which allow the time delays of the stimulation signals to be varied during the stimulation. Furthermore, the time delays can be varied, for example, not only within a stimulation period, but also as part of a number of periods. In this case, the stimulation signal corresponds to the neural activity which has been measured at a time earlier by a few periods.

7.2.3 Adaptation of the Intensity

The neural activity which represents the activity of the neuron population to be decoupled and/or of the driving neuron population is measured by a sensor 3. This neural activity is forwarded to unit 4 for signal processing and/or control. The unit 4 for signal processing and/or control performs a permanent or repetitive or demand-controlled stimulation according to section 6, wherein the intensity of the stimulation stimulus applied at the respective time depends on the instance of the pathological feature in the neural activity. For this purpose, the intensity of the stimulation stimulus can be preferably adapted. In this embodiment, the device comprises a control system which is programmed in such a manner that it varies the amplification of the measurement signals in accordance with section 3.3 for controlling the stimulus intensity. The relation between the stimulus intensity and instance of the pathological feature can be controlled either manually or automatically in dependence on the stimulation result. In a time window of freely selectable, preferably constant lengths which ends in a constant time interval before the respective stimulus, the instance of the pathological feature is determined in the following manner:

a) In the case where exclusively or predominantly the pathological activity to be decoupled and/or the driving pathological activity is measured via the sensor 3, the amplitude corresponds to the instance of the synchronization of the neuron population to be decoupled. The amplitude thus represents the pathological feature. The amplitude can then be estimated via the determination of the maximum of the signal or via the mean value of the amount of the signal or with band-pass filtering and/or with Hilbert transformation and/or wavelet analysis. The first two variants (determination of the maximum of the signal or determination of the mean value of the amount of the signal) are used especially preferably since the calculation of the amplitude by means of Hilbert transformation and/or wavelet analysis means a distinctly higher computational effort and their accuracy depends on the correct selection of algorithmic parameters.

b) If, in addition to the disease-specific activity, non-disease-specific activity, for example from other neuron populations, is measured via the sensor 3, the neural activity cannot be applied directly for estimating the instance of the pathological feature. Since the disease-specific activity occurs typically in a frequency range which differs from the frequency range of the non-disease-specific activity, the activity is preferably estimated in the disease-specific frequency range in this case. This is implemented, for example, by a frequency analysis. For example, the spectral energy in the disease-specific frequency range can be determined. As an alternative, after band-pass filtering, the amplitude can be determined by determining the maximum of the band-pass filtered signal or by determining the mean value of the amount of the signal and/or with Hilbert transformation and/or with wavelet analysis.

If the desired effect is not achieved, that is to say if the population to be decoupled is not adequately decoupled and thus the pathological feature of the neural activity is not shifted below the threshold value, the maximum intensity of the stimulus is slowly increased up to a maximum value rigidly predetermined for safety reasons, for example 5 V (e.g. in steps of 0.5 V per 50 periods). For this purpose, the device according to the invention has a control system which detects a change in the neural activity and, when the change in the neural activity disappears, adapts the stimulating signals towards upper values. After approx. 20 successful periods of stimulation, the device can begin to slowly correct the maximum intensity of the stimulus (e.g. in steps of 0.5 V per 50 periods) to lower values for as long as the stimulation result is still present. During this process, the stimulation result is determined as described above. The control system is programmed in such a manner that it detects the change in neural activity and thus the stimulation result. The maximum stimulus intensity is preferably controlled on a time scale between 10 and 1000 periods of the neural activity in such a manner that the neuron population to be decoupled is adequately decoupled and desynchronized.

Independently of the value of the stimulation intensity defined above, the amplitude of the resultant stimulation influence on the neuron population to be decoupled is automatically minimized due to the characteristics, described in section 5, of the stimulation mechanism of the device according to the invention after successful decoupling.

7.3 Stimulation Parameters for the Case Where the Electrode 2 is Not Located in the Neuron Population to be Decoupled As in the case described of an electrode 2 not located in the neuron population to be decoupled, the neuron population to be decoupled is influenced via an indirect stimulation as described in section 4.1. Since in the case of an indirect stimulation, the conduction times between the stimulated target population, on the one hand, and the population to be decoupled, on the other hand, can be of different magnitude in each case, the respective conduction times are first measured before the decoupling stimulation is carried out. For this purpose, a stimulus is applied via the stimulation electrode 2 and the response to the stimulus is measured via the sensors 3 placed in the neuron population to be decoupled. This is carried out L-times, where L is typically a small integral number of up to, for example, 200. From this, the mean conduction time is preferably estimated in the following manner:

The duration between the beginning of the application of the stimulus via the electrode 2 and the first maximum of the response to the stimulus or of the amount of the response to the stimulus $\tau(k)$ is determined for each individual stimulus application. In $\tau(k)$, the index k stands for the kth applied stimulus. From this, the mean duration between stimulus beginning and stimulus response is then determined separately for the stimulation electrode 2 via which the stimulation is indirectly applied, in accordance with the following formula 1:

$$\overline{\tau} = \frac{1}{L}\sum_{k=1}^{L}\tau^{(k)} \qquad \text{Formula 1}$$

where L is the number of the stimuli applied via the stimulation electrode 2.

For the stimulation, the conduction time $\overline{\tau}$ determined in this manner is taken into consideration in the following manner:

If, in the case of direct stimulation of the neuron population to be decoupled, a stimulus would be applied with a time delay t via the stimulation electrode 2, in the case of indirect stimulation the stimulus is imparted with a time delay t-$\overline{\tau}$ via the stimulation electrode 2, where t must be greater than $\overline{\tau}$ which can be achieved in accordance with section 7.2.2.

The determination of the stimulation parameters at the beginning of the stimulation, and the control mechanisms during the stimulation, are carried out completely analogously as described in sections 7.1 and 7.2, taking into consideration the conduction times $\overline{\tau}$ as described above.

8 Examples and Other Embodiments of the Device

8.1 Examples

For example, the following stimulus can be delivered via the electrode:

1. Via the electrode, a stimulation stimulus is applied which consists of two components: the feedback stimulation signal, i.e. the processed neural activity, where the stimulation signal is offset in time by T/2, where T is the mean period of the oscillations of the neuron population to be decoupled. The non-time-delayed processed neural activity is added to this signal. Together, they form the stimulation stimulus, see FIG. 2.
2. Via the electrode, a signal is applied which consists of three components: the processed and non-time-delayed neural activity is squared and multiplied by a neural activity time delayed by T/2 and processed, where T is the period of the rhythm of the driving neuron population, see FIG. 3.

The effect of the stimulation on the population to be decoupled becomes apparent in a reduction in the amplitude of the neural activity measured, see FIG. 2*a* and 3*a*, where the firing pattern of the neurons distinctly differs from the firing pattern in the pathological state, see FIG. 2*b* and 3*b*. This stimulation influence is also reflected in the extent of synchronization of the neuron population to be decoupled, see FIG. 2*c* and 3*c* which represents a confirmation that desynchronization of the population to be decoupled is occurring. In this process, the amplitude of the resultant stimulation influence, i.e. of the sum of coupling and stimulation, is automatically reduced and minimized due to the self-regulating demand control of the stimulation signal, described in section 5, see FIG. 2*d* and 3*d*. Furthermore, there is no influence on the inherent dynamics of the neurons during the stimulation which confirms that the inherent frequencies of the neuron population are distributed in FIG. 2*e* and 3*e*. Inherent frequencies are understood to be the frequencies of the neurons in the state without interaction and without stimulation. This confirms that optimum decoupling and desynchronization of the neuron population to be decoupled has occurred due to the stimulation according to the invention and the population has thus returned into its normal functional state which allows a considerable reduction in the disease-related symptoms to be expected.

For example, three different control mechanisms of the stimulus application, described in section 6, are used for stimulating by means of which preferably a demand-controlled, and thus energy-saving and mild stimulation (avoiding side effects) is made possible as described in section 7:

1. Permanent stimulus application: stimulation is applied permanently, preferably with adaptation of the stimulation period. Directly after application of the stimulation, decoupling and desynchronization of the neuron population to be decoupled occurs. This minimizes the amplitude of the neural activity measured. At the same time, the amplitude of the resultant influence of stimulation on the population to be decoupled is minimized due to the mechanism of self-regulating demand control described in section 5. After the stimulation has been switched off, a resynchronization may occur after a short time due to the pathological interaction between the populations.
2. Repetitive stimulus application, preferably with demand-controlled stimulus intensity: stimulation is applied repeatedly. In this process, the intensity of the stimuli is adapted to the intensity of the synchronization of the neuron population: the stronger the coupling and/or synchronization, the stronger the coordinated stimulus will be.

In this variant, $\tau/2$ can be preferably selected instead of T/2 as time delay, where T is the period of the rhythm without stimulation and T is the period enforced on the rhythm by stimulation. In other words: $1/\tau$ is the frequency of the stimulation signal with which the individual stimuli are applied. As a result, the only critical stimulation parameter is forced onto the system: instead of determining this parameter in a suitable manner as part of an elaborate calibration, it is dictated by the stimulation. In addition, this form of demand-controlled stimulation makes use of the circumstances that the neurons in the affected areas have a (pathological) tendency for periodically firing or bursting (rhythmic production of bursts of action potentials). For this reason, an entrainment of the neural activity of the neuron population to be decoupled can be achieved with respect to the enforced frequency.

3. Demand-controlled stimulus application (i.e. demand-controlled choice of starting and end times of the stimulation) of the stimulation stimulus: if the synchronization of the nerve cell population exceeds a threshold value, the next stimulus is delivered via the electrode as described in section 6.3.

In all three control methods described by way of example above, a self-regulating demand control, described in section 5, necessitates minimization of the energy input into the population to be decoupled. In this process, the only important stimulation parameters, the stimulation period T and thus the time delays, can be preferably adapted by measuring the frequency of the nerve cell population in the neuron population to be decoupled and/or the driving neuron population or another nerve cell population closely connected thereto.

The possibility exists of combining a number of stimulation electrodes in one stimulation electrode to be implanted, e.g. by positioning the stimulation contacts at different distances from the end of the electrode. This makes it possible to achieve a stimulation of the area to be decoupled which is as comprehensive as possible.

8.2 Other Embodiments of the Device

The device according to the invention can also be used for desynchronizing a pathologically synchronous neuron population. In this embodiment of the device according to the invention, a pathologically synchronous neuron population, e.g. the driving neuron population to be desynchronized, is desynchronized by means of stimulation with the feedback stimulation signal according to the invention. The characteristics of the device described above and the stimulation methods for decoupling the neuron population to be decoupled also apply to this embodiment of the device with the modification that the stimulation is applied in the neuron population to be desynchronized.

If the aim is desynchronization, this can be achieved by means of an arrangement of the stimulation electrode 2 according to section 4.1. A direct and indirect arrangement of the sensors 3 is also possible. In this case, the sensors 3 must be arranged in such a manner that a detection of the neural activity of the area to be desynchronized is possible. The details of this arrangement correspond to the details described in section 4.2 wherein the activity to be desynchronized is now measured. The pathologically synchronous activity of the neuron population to be desynchronized is measured directly and/or indirectly and processed according to section 3. This generates a stimulation signal which is used as basis for the stimulation stimuli. The stimulation stimuli generated are applied to the area to be desynchronized by means of a stimulation electrode so that direct or indirect stimulation of the population to be desynchronized occurs according to section 3 and 4.1 and the driving population is desynchronized according to the invention and the pathological symptoms are suppressed. If present, the driving coupling to the driven neuron population is also decoupled automatically due to the desynchronization of the driving population, i.e. due to the desynchronization of the driving neuron population, the pathological drive of the driven neuron population disappears. Due to the relationship of the stimulation signal with the neural activity of the neuron population to be desynchronized, the amplitude of the resultant influence of the stimulation on the population to be desynchronized, i.e. the amplitude of the stimulation signal in the present case (see section 2), is automatically minimized as described in section 5.

The arrangement of the electrode and sensors adapted to the aim of the stimulation according to section 4, all three control methods of controlling the stimulus application according to section 6, and the calibration and adaptation of the parameters according to section 7 can also be used for the embodiment of the device according to the invention described.

The device can also be used for decoupling a neuron population which is driven by a non-synchronous pathological neuron population. Furthermore, the device can be used for decoupling a population which is driven by a pathological activity and itself exhibits a non-pathological synchronous activity in the decoupled case. In this case, the arrangement of the electrode and sensors are identical with the arrangements described in section 4. The detection and processing of the neural activity is also effected in accordance with section 3.

Furthermore, the device can be used for eliminating or suppressing the coupling of a non-pathological area. This could be used, e.g. in the examination of the interaction of neuron populations. The detection and processing of the neural activity and the arrangement of the electrode and sensors occurs here in accordance with sections 3 and 4.

If, as mentioned in the introduction, a bilateral stimulation is necessary for decoupling the pathological activity, stimulation is preferably applied bilaterally with two individual devices or with one device according to the invention designed for this purpose which can forward signals to at least two stimulation electrodes.

9 Advantages

The device according to the invention has a number of advantages in comparison with existing devices, e.g. DE 103 18 071.0-33 "Device for desynchronizing neural brain activity":

1. The main advantage of the device according to the invention consists in that a physiological stimulus, namely the feedback stimulation signal, that is to say the measured and processed neural activity of the neuron population to be decoupled and/or of the neuron population to be desynchronized is used for the stimulation. As a result, the self-regulating demand control of the stimulation signal, described in section 5, occurs which minimizes the energy input into the neuron population to be decoupled or into the neuron population to be desynchronized and leads to slight side effects.
2. Due to the self-regulating stimulation signals according to section 5, the operation of the device according to the invention saves energy since both an energy-saving signal is used for the stimulation due to the demand-controlled stimulation signals and energy saving can be expected in the control devices according to the invention necessary for the stimulation control. As a result, the intervals between the necessary battery changes which are exhausting for the patient can be longer.
3. The embodiment of repetitive or permanent application with demand-controlled stimulus intensity is particularly advantageous since no threshold needs to be detected in this method. As a result, this embodiment can be implemented by means of much more simple algorithms. Correspondingly, their software or hardware implementation is much less complex.
4. In the case of permanent and repetitive stimulation with demand-controlled stimulus intensity and direct stimulation of the neuron population to be decoupled or of the neuron population to be desynchronized, no calibration is necessary, i.e. it is not necessary to perform a series of test stimuli in which the stimulation parameters are systematically varied, which leads to a reduced duration of the calibration.
5. Of great advantage overall is the general tolerance and ruggedness of the device according to the invention compared with the estimation of the parameters such as intensity, stimulation period and time delays.
6. By using only one electrode, the operative complexity, and thus the risk of complication during the operation, is considerably reduced for the patient. As a result, the device according to the invention provides a much gentler stimulus application.
7. Since the area to be decoupled is preferably located close to the surface of the brain, e.g. in the motor cortex, the access to the areas to be stimulated is much easier and with less risk, e.g. without depth implementation of the stimulation electrode.
8. The device can also be used for decoupling non-pathological activity and thus provides a novel and important possibility for examining the interaction of neural populations in the brain.

The lack of time-consuming calibration and the stability of the effect even with relatively great frequency fluctuations—particularly in method 1 of controlling the stimulus application (permanent stimulation, see section 6.1)—has important consequences.

1. The stimulation result can be checked immediately even intraoperatively during replacement of the electrode. As a result, the finding of the suitable target points can be clearly improved. The previous demand-controlled methods need calibration which lasts longer than 30 minutes per electrode. This cannot be carried out intraoperatively and cannot be expected of the patient (who is not anesthetized).

2. The new stimulation methods can also be used in neurological or psychiatric diseases in which the pathological rhythms have greatly fluctuating frequencies. In particular, the new methods can also be used for decoupling rhythms occurring intermittently (i.e. for short periods). The result is that the new stimulation methods can be used in far more diseases, especially also in the case of epilepsies.

Using the device according to the invention, the following diseases or symptoms can be treated with the new stimulation method by decoupling suitable brain areas.

In all neurological or psychiatric diseases in which pathological neural synchronization plays a role relevant for the instance of the disease-specific symptoms, for example: Parkinson's disease, essential tremor, dystonia, compulsive diseases, tremor in multiple sclerosis, tremor as a consequence of a stroke or other tissue damage, for example tumorous tissue damage, for example in the area of the thalamus and/or of the basal ganglia, choreoathetosis and epilepsy, this enumeration not being intended to be restrictive.

In the standard method currently used, continuous high-frequency stimulation, the following target areas are used, for example:

Nucleus subthalamicus in the case of Parkinson's disease or the thalamus in the case of tremor-dominant Parkinson's disease, for example the nucleus ventralis intermedius thalami.

In the case of essential tremor, the thalamus, for example the nucleus ventralis intermedius thalami.

In the case of dystonia and choreoathetosis, the globus pallidum internum, in the case of epilepsy, the nucleus subthalamicus, the cerebellum, thalamic core regions, for example the nucleus ventralis intermedius thalami, or the nucleus caudatus.

In the case of compulsive diseases, the capsula interna or the nucleus accumbens.

In the device according to the invention, for example, the target areas listed above for the respective diseases and/or areas coupled thereto can be selected. Because the device according to the invention either does not need calibration or the calibration can be carried out very rapidly, the possibility exists to test as part of the electrode implantation alternative target areas in which the decoupling effect and/or the desynchronizing effect of the device according to the invention can be developed even better.

The invention also comprises a control system which controls the operation of the device according to the invention as specified, and the use of the device and of the control system for treating the diseases Parkinson's disease, essential tremor, dystonia, compulsive diseases, choreoathetosis, tremor in multiple sclerosis, tremor as a consequence of a stroke or of other tissue damage, for example tumorous tissue damage, for example in the area of the thalamus and/or of the basal ganglia, and epilepsy.

The device according to the invention can be used both as implant for permanent therapy of the above-mentioned neurological and psychiatric diseases and for intraoperative target diagnostics, i.e. intraoperatively finding the optimum target point for the electrode implantation.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A device for decoupling and/or desynchronizing neural brain activity, comprising:
   at least one sensor to measure at least one signal which reproduces the development in time of activity of neuron population to be decoupled and/or of neuron population to be desynchronized;
   one electrode shank with at least one electrode surface; and
   a control system configured to receive measurement signals of the sensor, to process the measurement signals, and to feed the processed measurement signals as stimulation signals into the electrode shank, the processing of the measurement signals consisting of one or more of filtering the measurement signals, delaying the measurement signals, amplifying the measurement signals, and changing the polarity of the measurement signals.

2. The device as claimed in claim 1, wherein
   the control system measures the variation with time of the activity of the neuron population to be decoupled and/or to be desynchronized directly and/or indirectly via the sensors, or
   the control system measures via at least one of the sensors the variation with time of the activity of a muscle group influenced by the area to be decoupled and/or to be desynchronized and/or the variation with time of the activity of a neuron population associated with the area to be decoupled and/or to be desynchronized.

3. The device as claimed in claim 2, wherein
   the control system measures the variation with time of the activity permanently, or, in time-limited measurement intervals, the control system, in a measurement in time-limited measuring intervals, controls the duration and/or the intervals of the limited measurement intervals by means of a deterministic and/or stochastic and/or combined stochastic/deterministic algorithm, and/or
   the control system stores the measurement signals.

4. The device as claimed in claim 1, wherein
   the control system contains additional demand control.

5. The device as claimed in claim 4, wherein
   the control system uses the measurement signals and/or the stimulation signals for the demand control, and/or
   the control system detects a pathological feature in the measurement and/or stimulation signal, and/or
   the control system uses the amplitude of the measurement and/or stimulation signal for the demand control, and/or
   the control system estimates the amplitude of the measurement and/or stimulation signal by using the signal itself and/or the absolute value of the signal and/or the signal which is band-pass-filtered in the disease-specific frequency range and/or the absolute value of the signal which is band-pass-filtered in the disease-specific frequency range and/or the instantaneous amplitude determined by Hilbert transformation and/or wavelet analysis, and/or
   the control system, when detecting a pathological feature in the measurement and/or stimulation signal, applies a stimulation stimulus, and/or
   the control system detects a pathological feature by detecting the transgression of a threshold value of the amplitude of the measurement and/or stimulation signal, and/or
   the control system detects a pathological feature by detecting the transgression of a threshold value of the amplitude of the measurement signal, which is band-passfiltered in the disease-specific frequency range, and/or of the stimulation signal, and/or the control system, for detecting a pathological feature, compares the amplitude of the measurement and/or stimulation signal with the threshold value in a sliding time window.

6. The device as claimed in claim 1, wherein the control system changes the parameters of the stimulation signals.

7. The device as claimed in claim 6, wherein the control system changes the parameters of the stimulation signals by adapting the stimulation period T to the instantaneous period of the neuron population to be decoupled and/or to be desynchronized, or the control system determines the instantaneous period either by estimating the time difference of trigger points or by means of frequency estimators, and/or the control system changes the parameters of the stimulation signals by adapting the stimulation period T to the mean frequency of the neuron population to be decoupled and/or to be desynchronized, and/or the control system changes the parameters of the stimulation signals by adapting the time delay of the stimulation signals to the stimulation period T, and/or the control system changes the parameters of the stimulation signals by adapting the stimulus intensity, or the control system controls the stimulus intensity on a time scale between 10 and 1000 periods of the neural activity, in such a manner that adequate decoupling and/or desynchronization occurs, and/or the control system varies the amplification of the measurement signals for controlling the stimulus intensity, and/or the control system is programmed in such a manner that the relation between stimulus intensity and instance of the pathological feature can be adjusted either manually and/or is controlled automatically in dependence on the stimulation result.

8. The device as claimed in claim 1, wherein the control system contains an additional manual demand control, and/or the control system arranges the measurement and stimulation intervals to overlap or at the same time or separately in time, and/or the control system stimulates the neuron population to be decoupled and/or to be desynchronized either directly or indirectly via the electrode, or the control system stimulates a neuron population connected via nerve fiber bundles with the neuron population to be decoupled and/or to be desynchronized and/or stimulates a nerve fiber bundle, connected to the neuron population to be decoupled and/or to be desynchronized, via the electrode, and/or the control system detects differences in the conduction time between the stimulation location of the electrode and the location of the neuron population stimulated by it, and/or the control system when calculating the time delays of the stimulation signals and/or when processing the measurement signals, also calculates in the associated conduction times, and/or the electrode is constructionally combined with at least one sensor, and/or a DC isolation exists between the control system and the electrodes, and/or the device is connected to means for displaying and processing the measurement and/or stimulation signals and for saving data via a telemetry transmitter and a telemetry receiver, and/or the device is connected to an additional reference database via a telemetry transmitter and a telemetry receiver.

9. A method for use of the device as claimed in claim 1 for finding the target for the stimulation.

* * * * *